United States Patent
Matsuda et al.

(10) Patent No.: US 8,481,330 B2
(45) Date of Patent: Jul. 9, 2013

(54) METHOD FOR ANALYZING SAMPLE SOLUTION AND APPARATUS FOR ANALYZING SAMPLE SOLUTION

(75) Inventors: Yoko Matsuda, Ehime (JP); Mie Takahashi, Ehime (JP); Masahiro Aga, Ehime (JP); Hideyuki Kurokawa, Ehime (JP); Takahiko Tanida, Ehime (JP); Ryosuke Yamada, Ehime (JP)

(73) Assignee: Panasonic Corporation, Osaka (JP)

( * ) Notice: Subject to any disclaimer, the term of this patent is extended or adjusted under 35 U.S.C. 154(b) by 357 days.

(21) Appl. No.: 12/863,070

(22) PCT Filed: Jan. 9, 2009

(86) PCT No.: PCT/JP2009/000060
§ 371 (c)(1),
(2), (4) Date: Jul. 15, 2010

(87) PCT Pub. No.: WO2009/090861
PCT Pub. Date: Jul. 23, 2009

(65) Prior Publication Data
US 2011/0053291 A1    Mar. 3, 2011

(30) Foreign Application Priority Data

Jan. 16, 2008  (JP) ................................. 2008-006343

(51) Int. Cl.
*G01N 21/03*   (2006.01)

(52) U.S. Cl.
USPC ........... 436/165; 436/518; 436/164; 436/174; 436/166

(58) Field of Classification Search
USPC ................. 436/518, 536, 161, 164, 165, 166, 436/174, 180
See application file for complete search history.

(56) References Cited

U.S. PATENT DOCUMENTS

| 5,403,551 A | * | 4/1995 | Galloway et al. | 422/417 |
| 5,916,815 A | * | 6/1999 | Lappe | 436/92 |
| 6,372,514 B1 | * | 4/2002 | Lee | 436/518 |

(Continued)

FOREIGN PATENT DOCUMENTS

| EP | 0166878 | 1/1986 |
| JP | 11-051967 | 2/1999 |

(Continued)

OTHER PUBLICATIONS

International Search Report of PCT/JP2009/000060, dated Feb. 3, 2009.

*Primary Examiner* — Melanie Y Brown
(74) *Attorney, Agent, or Firm* — Hamre, Schumann, Mueller & Larson, P.C.

(57) ABSTRACT

Disclosed is a method for analyzing a sample solution, including introducing a sample solution 50 through a sample introduction part 6 and developing the sample solution 50 to a developing layer 2 through a capillary phenomenon to analyze an analyte contained in the sample solution 50, the sample introduction part 6 being provided on one side of a test strip 100 and the developing layer 2 being provided on the other side of the test strip 100, wherein the test strip 100 is disposed in such a development posture that the downstream region of the developing layer faces downward during the development. By this method, the developing rate is less susceptible to the viscosity of the sample solution 50 and thus has a small difference even among sample solutions 50 differing in viscosity. As a result, the analytical accuracy and reliability can be improved.

5 Claims, 11 Drawing Sheets

U.S. PATENT DOCUMENTS

| | | | |
|---|---|---|---|
| 7,090,803 B1 * | 8/2006 | Gould et al. | 422/413 |
| 8,021,625 B2 * | 9/2011 | Wang et al. | 422/414 |
| 2003/0205097 A1 | 11/2003 | Wickstead et al. | |
| 2005/0009203 A1 * | 1/2005 | Wong | 436/518 |
| 2005/0106750 A1 * | 5/2005 | Tung et al. | 436/169 |
| 2006/0029517 A1 * | 2/2006 | Hartselle | 422/61 |
| 2006/0062688 A1 | 3/2006 | Lawrence | |

FOREIGN PATENT DOCUMENTS

| | | |
|---|---|---|
| JP | 2004-517325 | 6/2004 |
| JP | 3655283 | 3/2005 |
| JP | 2005-515431 | 5/2005 |
| JP | 3813150 | 6/2006 |
| WO | 01/92886 | 12/2001 |
| WO | 02/056019 | 7/2002 |
| WO | 03/014741 | 2/2003 |
| WO | 2005/074609 | 8/2005 |
| WO | 2007/065695 | 6/2007 |
| WO | WO 2007/065695 | 6/2007 |

* cited by examiner

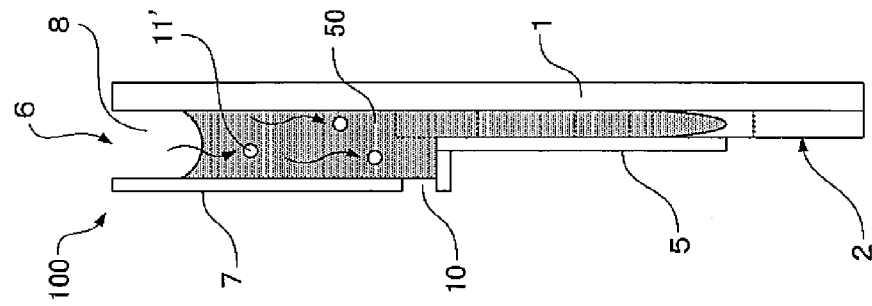
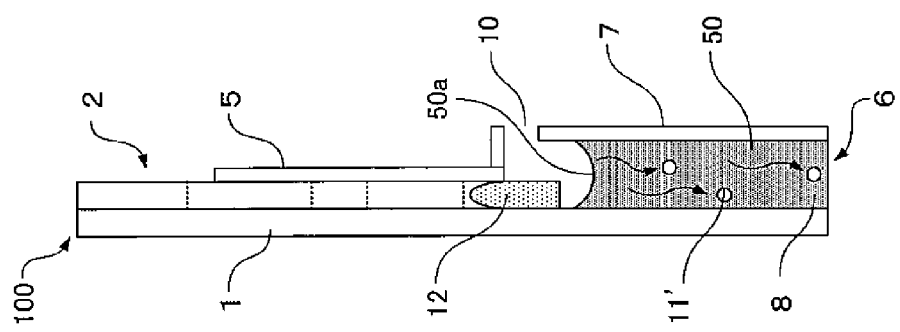
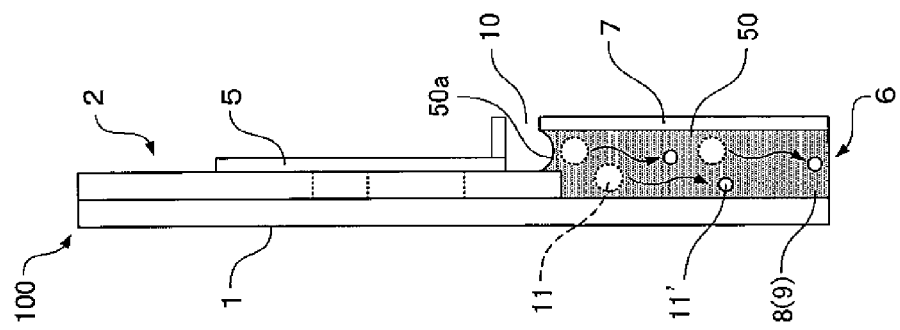

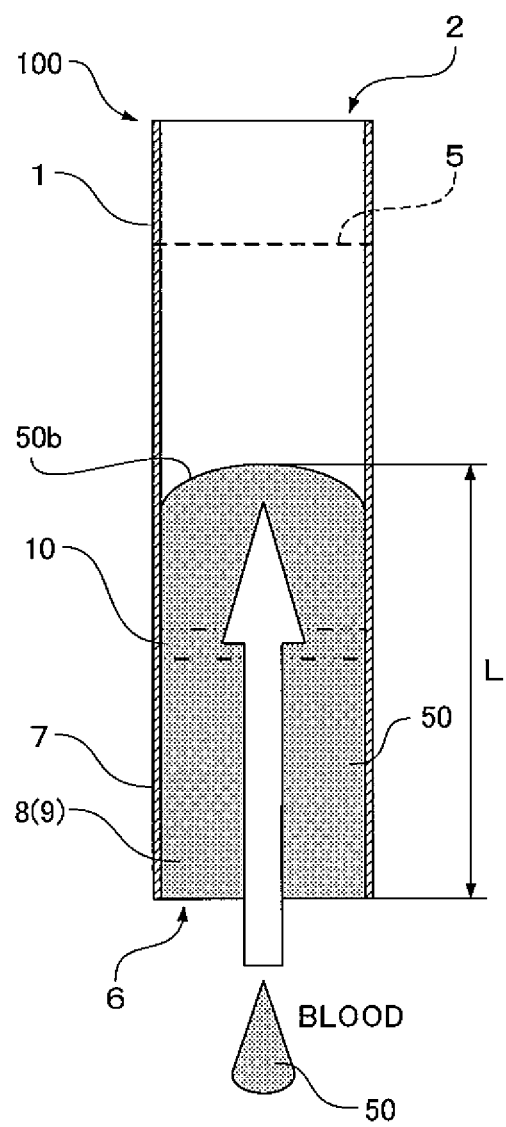

US 8,481,330 B2

METHOD FOR ANALYZING SAMPLE SOLUTION AND APPARATUS FOR ANALYZING SAMPLE SOLUTION

TECHNICAL FIELD

The present invention relates to a method for analyzing a sample solution, including developing a sample solution to a developing layer in a test strip through a capillary phenomenon to analyze an analyte contained in the sample solution, and to an apparatus for analyzing a sample solution using this method for analyzing a sample solution.

BACKGROUND ART

With expansion of home care and community medicine (doctors' offices, clinics, etc.) and growing numbers of early diagnoses and highly urgent clinical laboratory tests, etc., even persons other than clinical laboratory test experts have demanded, in recent years, an analysis apparatus capable of simply and rapidly performing highly precise measurement. Thus, an analysis apparatus intended for POCT (Point of Care Testing) is in the limelight, which is capable of performing highly reliable measurement in a short time without complicated procedures. In general, POCT is a generic name for "near-patient" tests such as tests conducted in practitioners' or specialists' offices, wards, and outpatient clinics. This method attracts attention as being highly useful for improving the quality of clinical practice because the doctor can make an on-the-spot judgment on test results, perform rapid treatment, and even monitor a treatment process or prognosis. The POCT can reduce costs required for transportation of samples or for facilities or costs required for unnecessary tests, compared with tests conducted in the central laboratories of hospitals or the like, and can allegedly cut back on total amounts of test costs. The POCT market has rapidly expanded in the U.S. with progress in the streamlining of hospital management and is expected to grow worldwide, including Japan.

Dry analysis devices typified by chromatographic test strips as immunosensors are capable of analyzing an analyte in a test solution only by simple procedures such as dropwise addition of a sample solution (e.g., blood or urine) to be measured onto the analysis device, without the need of preparing reagents, and are very useful for a convenient and rapid analysis. Therefore, a large number of such devices are now put in practical use as a representative of POCT. Moreover, the market demands more highly precise measurement in a shorter time, in addition to measurement that can be achieved anytime and anywhere by anyone. Also, analysis apparatuses have been proposed, which specialize in optical reading from the analysis devices.

Hereinafter, a conventional method for measuring an immunochromatographic test strip will be described. When a sample solution containing a cellular component is analyzed by a conventional approach, a structure which removes the cellular component in advance or a structure having a cellular component separating member provided in a chromatographic test strip is required. However, such a method disadvantageously requires a time for removing the cellular component in advance or disadvantageously requires the sample solution in non-small amounts in consideration of samples absorbed in the cellular component separating member. Thus, as disclosed in Japanese Patent Nos. 3655283 and 3813150, a method has been proposed, which includes contracting a cellular component and then developing a sample solution.

FIGS. 10(a) and 10(b) are an exploded perspective view and a perspective view, respectively, of a conventional immunochromatographic test strip. FIGS. 11(a) and 11(b) are respectively a cross-sectional view of the immunochromatographic test strip, wherein FIG. 11(a) is a diagram showing an image of red blood cells in a gap portion after blood introduction, and FIG. 11(b) is a diagram showing an image of the mixed state of plasma and a labeling reagent in the gap portion after plasma introduction.

An immunochromatographic test strip (hereinafter, simply referred to as a test strip) 100 using an antigen-antibody reaction includes: a gap portion 8 formed by a transparent space forming member 7 which is provided on one side in the longitudinal direction of the test strip 100, has an air vent 10, and holds a cell shrinkage reagent 9 capable of being eluted due to a sample solution 50; a developing layer 2 which is provided to extend from the central part in the longitudinal direction of the test strip 100 to the other side of the test strip and develops the sample solution 50 through a capillary phenomenon; a developing layer support 1 which is provided in the whole area in the longitudinal direction of the test strip 100; a labeling reagent holding part 3 which contains a substance (e.g., a colloidal gold labeling reagent) specifically binding to an analyte contained in the sample solution 50 flowing to the upstream region of the developing layer 2; a reagent-immobilized part 4 which immobilizes the analyte bound with the labeling reagent; a liquid absorption part 19 which finally absorbs the sample solution 50; a transparent liquid-impermeable sheet 5 which covers the developing layer 2; and so on. Reference numeral 6 in FIGS. 10 and 11 depicts a sample introduction part which introduces a sample solution therethrough, and this sample introduction part is formed by an opening at the end of the gap portion 8. The amount of the labeling reagent immobilized on the reagent-immobilized part 4 can be measured to thereby determine the concentration of the analyte in the sample solution 50.

In this context, as shown in FIGS. 10(b) and 11(a), the test strip 100 is kept in a horizontal posture, while the sample solution is introduced to the sample introduction part 6 and subjected to a reaction or development.

Specifically, when blood as an example of the sample solution 50 is introduced to the sample introduction part 6, the sample solution 50 reacts with the cell shrinkage reagent 9 in the gap portion 8. Then, the sample solution 50 flows through the developing layer 2 and elutes a colloidal gold labeling reagent in the labeling reagent holding part 3. Next, by this elution of the labeling reagent, a colloidal gold-labeled antibody and an analyte (antigen) contained in the sample solution cause a binding reaction during which the reaction solution further flows through the developing layer 2 and arrives at the reagent-immobilized part 4. Then, the complex of the colloidal gold-labeled antibody and the antigen binds to an antibody immobilized in the developing layer 2. Through these processes, a color of the colloidal gold appearing in the reagent-immobilized part 4 can be detected by visual observation or using an optical detector to thereby confirm the presence or concentration of the analyte in the sample solution 50. In the test strip 100, the gap portion 8 formed by the space forming member 7 holds the cell shrinkage reagent 9, which in turn contracts red blood cells as a cellular component in blood into a size smaller than the pores of the developing layer 2. As a result, the whole blood is favorably developed to the developing layer 2.

DISCLOSURE OF THE INVENTION

Problems to be Solved by the Invention

However, the conventional method for analyzing a sample solution as shown in FIGS. 10 and 11 has a large difference (variations) in the developing rate of a sample solution 50 (e.g., blood) travelling in a developing layer 2 in a test strip 100 supported in a horizontal posture, due to the viscosity of the sample solution 50 (e.g., a hematocrit having positive correlation with the viscosity of blood). Thus, blood having a larger viscosity is disadvantageously much slower in developing rate than blood having a smaller viscosity. As a result, not only does the development time or analysis time become longer, but also the whole amount of a sample solution 50 (e.g., blood having an exceedingly large viscosity) may not arrive at a reagent-immobilized part 4 yet even when the analysis time is set to a certain amount of extra time added to a development time with respect to a sample solution 50 having a standard viscosity. Moreover, the amount of the analyte passing through the reagent-immobilized part 4 within the analysis time is larger at a faster developing rate and smaller at a slower developing rate. Therefore, the larger amount of the analyte flowing is measured with higher sensitivity, whereas the smaller amount of the analyte flowing is measured with lower sensitivity. Thus, this difference in measurement sensitivity deteriorates the analytical accuracy or reliability.

Moreover, in the conventional method for analyzing a sample solution, blood on the developing layer 2 side aspirated in a gap portion 8 (i.e., red blood cells 11' at this site) sufficiently reacts with a cell shrinkage reagent 9 as shown in FIG. 11(a), whereas blood on the sample introduction part 6 side (i.e., red blood cells 11 at this site) insufficiently reacts with the cell shrinkage reagent 9. This causes variations in the reaction state between blood and the reagent. Thus, blood insufficiently reacted with the cell shrinkage reagent 9 is developed to the developing layer 2. As a result, the analytical accuracy is disadvantageously deteriorated.

Moreover, when the sample solution 50 is plasma as shown in FIG. 11(b), the influence of red blood cells can be eliminated. However, the concentration of a labeling reagent eluted into plasma aspirated in the gap portion 8 is disadvantageously higher on the developing layer 2 side and lower on the sample introduction part 6 side. This causes variations in the reaction between plasma and the labeling reagent. Thus, plasma insufficiently reacted with the labeling reagent is disadvantageously developed to the developing layer 2.

An object of the present invention is to solve the problems of the conventional method and to provide a method for analyzing a sample solution and an apparatus for analyzing a sample solution, which can not only reduce an analysis time but also minimize deterioration in precision caused by different viscosities of sample solutions. Another object of the present invention is to provide a method for analyzing a sample solution and an apparatus for analyzing a sample solution, which secures a time sufficient for the reaction between a sample solution and a reagent (e.g., a cell shrinkage reagent) and achieves highly precise measurement of the sample solution even in trace amounts through a uniform reaction between the sample solution and the reagent.

Means for Solving the Problems

To attain the object, a method for analyzing a sample solution according to the present invention includes introducing a sample solution through a sample introduction part and developing the sample solution to a developing layer through a capillary phenomenon to analyze an analyte contained in the sample solution, the sample introduction part being provided on one side of a test strip and the developing layer being provided so that the downstream region of the developing layer extends to the other side of the test strip, wherein the test strip is disposed in such a development posture that the downstream region of the developing layer faces downward during the development.

By this method, since the test strip is disposed in such a development posture that the downstream region of the developing layer faces downward during the development, the developing rate of the sample solution is increased by means of gravity, compared with a test strip disposed in a horizontal posture even during development. As a result, the development time and analysis time can be reduced. In addition, since a force is added by means of gravity to the sample solution to move to the downstream region of the developing layer, the developing rate is less susceptible to the viscosity of the sample solution and thus has a small difference even among sample solutions differing in viscosity, compared with a test strip kept in a horizontal posture. As a result, a sample solution arrives in almost equal amounts at a predetermined site (e.g., a reagent-immobilized part) in the developing layer, regardless of the viscosity, when measurement is performed with the analysis time set to a certain amount of extra time added to a development time with respect to a sample solution having a standard viscosity. Thus, the amount of the analyte passing through the reagent-immobilized part within the analysis time does not differ among sample solutions. As a result, the analytical accuracy or reliability can be improved.

Moreover, in the method for analyzing a sample solution according to the present invention, the test strip is disposed in an introduction posture suitable for introducing the sample solution to the sample introduction part during the sample solution introduction, and the test strip is then shifted to such a development posture that the downstream region of the developing layer faces downward during the development.

By this method, since the sample can be introduced in an introduction posture that permits easy introduction of the sample solution to the sample introduction part during the sample solution introduction, improved convenience can be offered to a user.

Moreover, the method for analyzing a sample solution according to the present invention further includes arranging a reagent on the one side of the test strip, mixing the reagent with the introduced sample solution, and developing the sample solution thus mixed with the reagent to the developing layer to analyze an analyte contained in the sample solution, wherein the test strip is disposed in such a reaction posture that the one side of the test strip is positioned lower than the other side of the test strip during or after the introduction of the sample solution to the sample introduction part, and the test strip is then shifted to such a development posture that the other side of the test strip is positioned lower than the one side of the test strip. In this context, the reagent is any reagent such as a cell shrinkage reagent or a labeling reagent.

By this method, the test strip is disposed in such a reaction posture that the one side (where the sample introduction part or the reagent is provided) of the test strip is positioned lower than the other side of the test strip during or after the introduction of the sample solution to the sample introduction part. Accordingly, in this posture, the sample solution can be reserved favorably on the one side of the test strip. Thus, a time sufficient for the reaction between the reagent and the sample solution can be secured. As a result, a uniform reaction is achieved therebetween.

Moreover, in the method for analyzing a sample solution according to the present invention, the operation of disposing the test strip in the reaction posture after the introduction of the sample solution thereto and then the operation of shifting the test strip to the development posture are repetitively performed.

By repetitively performing the operation of disposing the test strip in the reaction posture and the operation of shifting the test strip to the development posture in this way, the reagent and the sample solution are more favorably stirred, compared with the reaction between a reagent and a sample solution in a test strip kept in a horizontal posture. As a result, a further favorable reaction can be achieved therebetween.

Moreover, the method for analyzing a sample solution according to the present invention further includes changeably arranging the posture of the test strip, detecting a position at which the sample solution arrives in the developing layer, and setting at least one of the posture of the test strip and duration of the posture based on the position.

By this method, since, according to the position at which the sample solution arrives in the developing layer, the posture of the test strip or a duration of the posture in the subsequent procedures is set, the development is further less susceptible to the viscosity of the sample solution. As a result, the analytical accuracy or reliability can be improved.

Moreover, in the method for analyzing a sample solution according to the present invention, the sample solution is blood.

Moreover, an apparatus for analyzing a sample solution according to the present invention includes a test strip having a sample introduction part which introduces a sample solution therethrough and a developing layer, the sample introduction part being provided on one side of the test strip and the developing layer being provided so that the downstream region of the developing layer extends to the other side of the test strip, the apparatus developing the sample solution in the developing layer through a capillary phenomenon to analyze an analyte contained in the sample solution, wherein the apparatus includes a test strip holding unit which holds the test strip, and a shift driving unit which shifts the test strip to an introduction posture suitable for introducing the sample solution to the sample introduction part and to such a development posture that the other side of the test strip is positioned lower than the one side of the test strip.

By this constitution, since the shift driving unit can be driven to favorably shift the test strip to the introduction posture or to the development posture and to dispose the test strip in such a development posture that the downstream region of the developing layer faces downward during the development, the development is less susceptible to the viscosity of the sample solution. As a result, the analytical accuracy or reliability can be improved.

Moreover, the apparatus for analyzing a sample solution according to the present invention further includes a reagent to be mixed with the sample solution, the reagent being provided on the one side of the test strip, wherein the shift driving unit shifts the test strip to such a reaction posture that the one side of the test strip is positioned lower than the other side of the test strip and to such a development posture that the other side of the test strip is positioned lower than the one side of the test strip.

By this constitution, since the shift driving unit can be driven to favorably shift the test strip to the reaction posture or to the development posture and to dispose the test strip in the reaction posture during the introduction of the sample solution to the sample introduction part, a time sufficient for the reaction between the reagent and the sample solution can be secured. As a result, a uniform reaction can be achieved therebetween.

Moreover, the apparatus for analyzing a sample solution according to the present invention further includes a detecting unit which detects a position at which the sample solution arrives in the developing layer in the test strip. By this constitution, the analysis can be achieved while the position at which the sample solution arrives in the developing layer is detected. As a result, the analytical accuracy or reliability can be improved.

Moreover, the apparatus for analyzing a sample solution according to the present invention further includes a controlling part which controls the posture of the test strip and duration of the posture based on the position at which the sample solution arrives in the developing layer. By this constitution, the sample solution can be controlled to be favorably developed in the developing layer. As a result, the analytical accuracy or reliability can be improved.

Moreover, in the apparatus for analyzing a sample solution according to the present invention, the shift driving unit rotates the test strip in a plane along a plane for detection of the test strip. The detecting unit is disposed so that its detection range is the plane along the plane for detection. In such a case, the deployed position of the test strip shifted to any posture can be detected favorably using one detecting unit.

Moreover, in the apparatus for analyzing a sample solution according to the present invention, the sample solution is blood.

Advantages of the Invention

According to a method for analyzing a sample solution and an apparatus for analyzing a sample solution according to the present invention, since a test strip is disposed in such a development posture that the downstream region of the developing layer faces downward during development, a sample solution can be developed in a manner less susceptible to the viscosity of the solution. As a result, the analytical accuracy or reliability can be improved.

Moreover, according to the method for analyzing a sample solution and the apparatus for analyzing a sample solution according to the present invention, since the test strip is disposed in such a reaction posture that one side of the test strip is positioned lower than the other side of the test strip during or after the introduction of the sample solution to a sample introduction part, a time sufficient for the reaction between the sample solution and the reagent can be secured. As a result, a uniform reaction can be achieved between the sample solution and the reagent. Thus, the sample solution even in trace amounts can be measured highly precisely.

BRIEF DESCRIPTION OF THE DRAWINGS

FIGS. 3(a) to 3(c) are respectively a side view schematically showing the method for analyzing a sample solution according to the embodiment 1 of the present invention, wherein FIG. 3(a) shows a state during sample solution introduction in the method for analyzing a sample solution, and FIGS. 3(b) and 3(c) respectively show a state during development in the method for analyzing a sample solution;

FIGS. 4(a) and 4(b) are respectively a cross-sectional side view showing the state of the test strip after a given time from sample solution introduction in the embodiment 1, wherein FIG. 4(a) shows as a comparative example that the test strip continues to stand still in a horizontal posture even after sample solution introduction, and FIG. 4(b) shows as the embodiment of the present invention that the test strip stands still in such a development posture that the downstream region of a developing layer faces downward after sample solution introduction;

FIG. 6 is an image of the behavior of red blood cells as a cellular component in a gap portion in the method for analyzing a sample solution according to the embodiment 2, wherein FIG. 6(a) shows a state immediately after sample solution introduction, FIG. 6(b) shows a state after a lapse of some time after sample solution introduction, and FIG. 6(c) shows a state during sample solution development;

FIGS. 7(a) to 7(c) are respectively a diagram schematically showing the structure of an apparatus for analyzing a sample solution according to the embodiment 2 of the present invention, wherein FIG. 7(a) is a perspective view of the apparatus for analyzing a sample solution, FIG. 7(b) is a side view of the apparatus for analyzing a sample solution immediately after blood introduction, and FIG. 7(c) is a side view of the apparatus for analyzing a sample solution after changing an angle at which a test strip is inclined;

FIG. 8 is a front view showing a position at which blood arrives in the test strip according to the embodiment 2 of the present invention;

FIG. 9 is an image of the mixed state of plasma as a sample solution and a labeling reagent in a gap portion in the test strip according to the embodiment 3, wherein

FIGS. 11(a) and 11(b) are respectively a cross-sectional view of the immunochromatographic test strip, wherein FIG. 11(a) is an image of red blood cells in a gap portion after blood introduction, and FIG. 11(b) is an image of the mixed state of plasma and a labeling reagent in the gap portion after plasma introduction.

BEST MODE FOR CARRYING OUT THE INVENTION

Hereinafter, a method for analyzing a sample solution and an apparatus for analyzing a sample solution according to embodiments of the present invention will be described in detail with reference to the drawings.

Embodiment 1

Figure 1A:
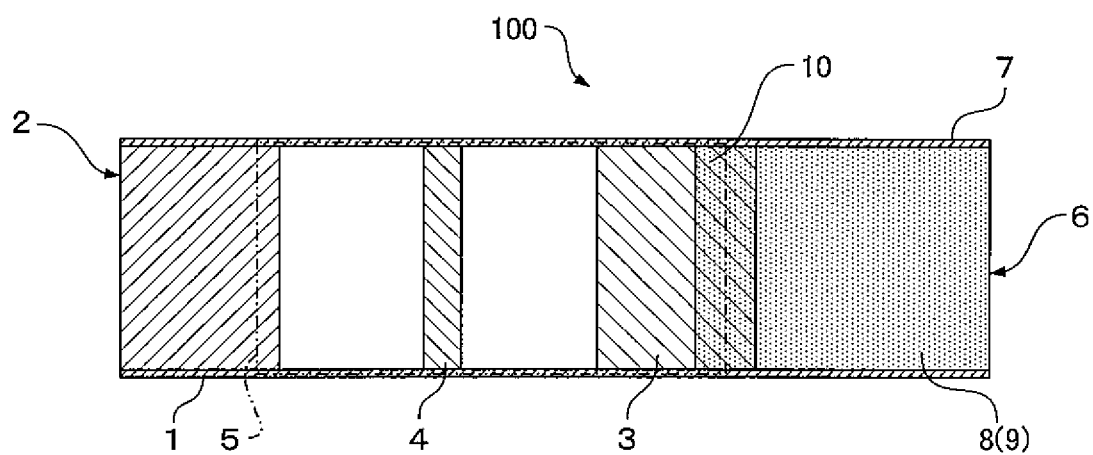
FIG. 1(a) is a plane view of a test strip used in a method for analyzing a sample solution according to an embodiment 1 of the present invention.
Figure 1B:
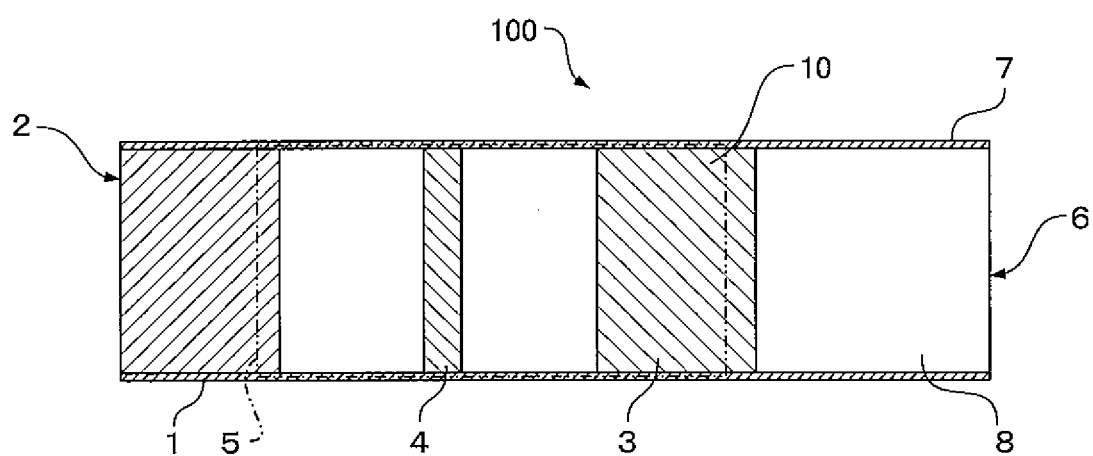
FIG. 1(b) is a plane view of a test strip used in a method for analyzing a sample solution according to an embodiment 3 of the present invention.
Figure 10A:
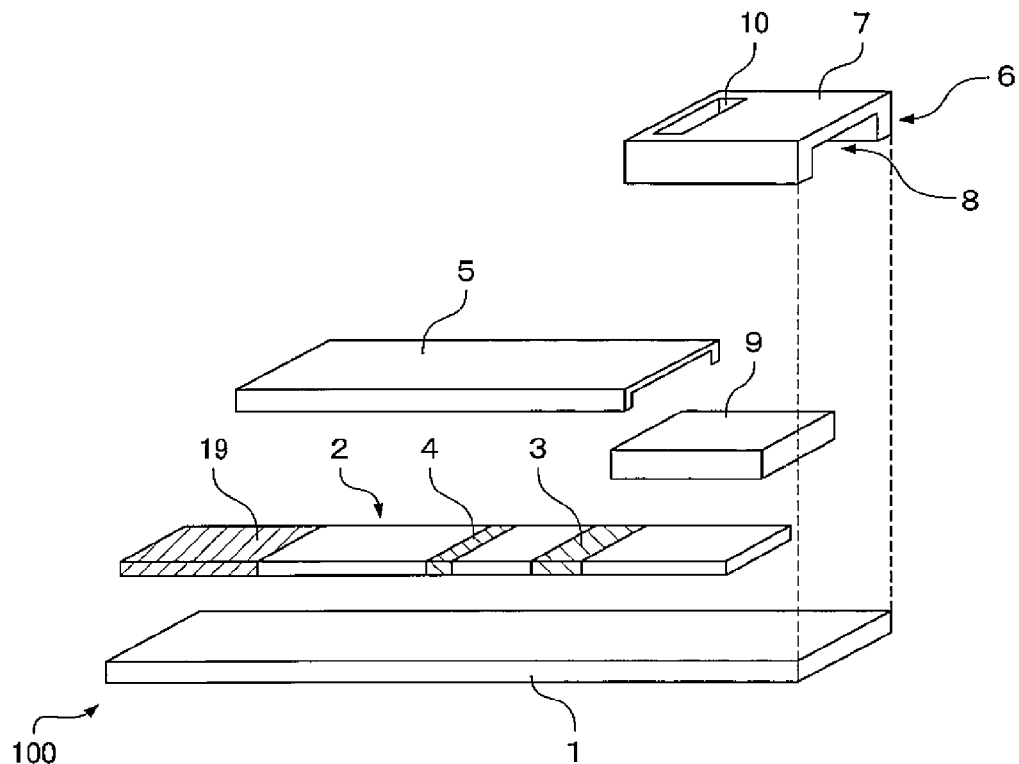
FIGS. 10(a) and 10(b) are an exploded perspective view and a perspective view, respectively, of a conventional immunochromatographic test strip.
Figure 10B:
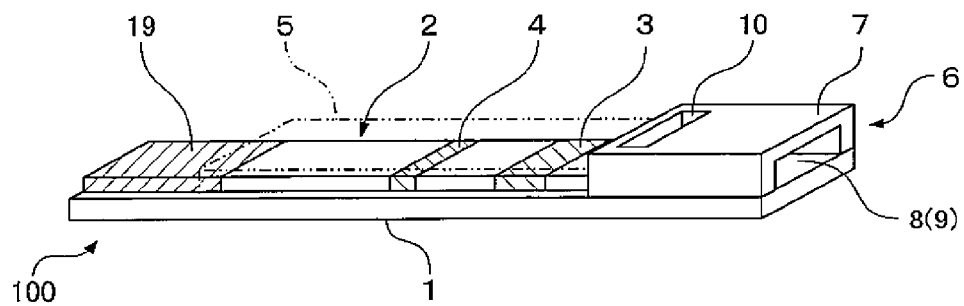
Figure 11A:
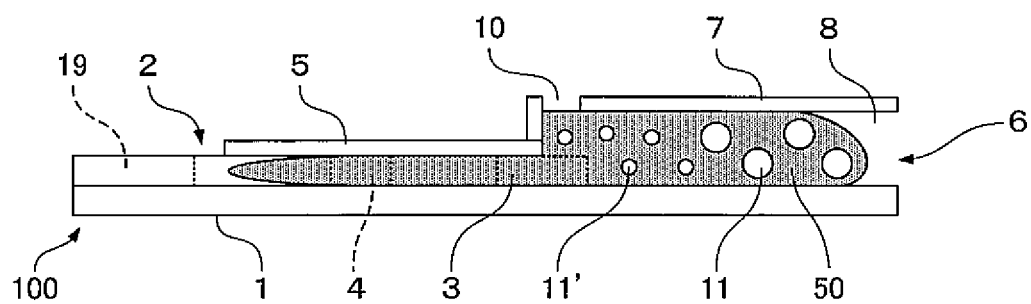
Figure 11B:
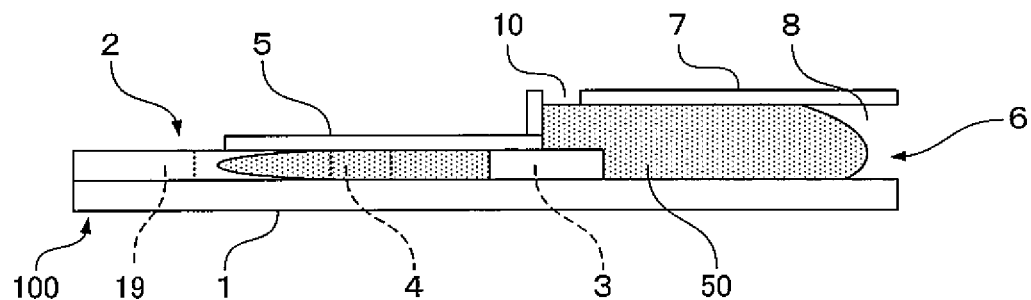

FIGS. 1(a) and 1(b) are respectively a plane view of a test strip used in a method for analyzing a sample solution according to an embodiment 1 of the present invention. A test strip 100 used in the method for analyzing a sample solution according to this embodiment of the present invention has the same constitution and functions as those of the immunochromatographic test strip 100 described in FIGS. 10(a) and 10(b). In this context, the same reference numerals will be used to designate components having the same or similar functions.

As shown in FIGS. 1(a) and 1(b), the test strip 100 includes: a gap portion 8 formed by a transparent space forming member 7 which is provided on one side in the longitudinal direction of the test strip 100, has an air vent 10, and holds a reagent 9 capable of being eluted due to a sample solution; a developing layer 2 which is provided to extend from the central part in the longitudinal direction of the test strip 100 to the other side of the test strip and develops the sample solution through a capillary phenomenon; a developing layer support 1 which is provided in the whole area in the longitudinal direction of the test strip 100; a labeling reagent holding part 3 which contains a labeling reagent specifically reacting with an analyte contained in the sample solution flowing to the upstream region of the developing layer 2; a reagent-immobilized part 4 which contains an immobilized reagent capable of specifically reacting with the complex of the analyte bound with the labeling reagent; a liquid absorption part 19 which finally absorbs the sample solution; and a transparent liquid-impermeable sheet 5 which covers the developing layer 2 to protect the sample solution (e.g., blood) from drying and assist in uniform development. In detail, a sample introduction part 6 formed by an opening at the end of the gap portion 8 is provided on the one side of the test strip 100. This gap portion 8 holds the cell shrinkage reagent 9, and the developing layer 2 is provided so that the downstream region of the developing layer 2 extends to the other side of the test strip 100. When a sample solution is introduced to the test strip 100, an analyte contained in the sample solution reacts with the labeling reagent or the immobilized reagent to generate a color of the labeling reagent in the reagent-immobilized part 4. This color is photographed using an image sensor 23 described later, and the color intensity in the reagent-immobilized part 4 is determined to thereby detect the concentration of the analyte.

Figure 2A:
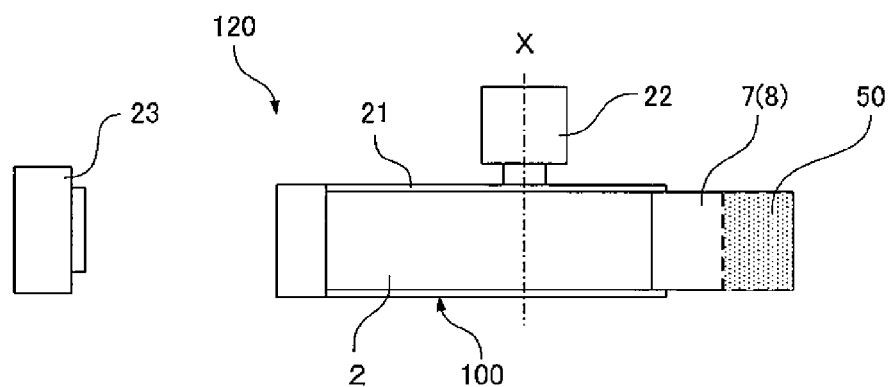
FIGS. 2(a) and 2(b) are a plane view and a side view, respectively, schematically showing an example of an apparatus for analyzing a sample solution according to the embodiment 1 of the present invention.
Figure 2B:
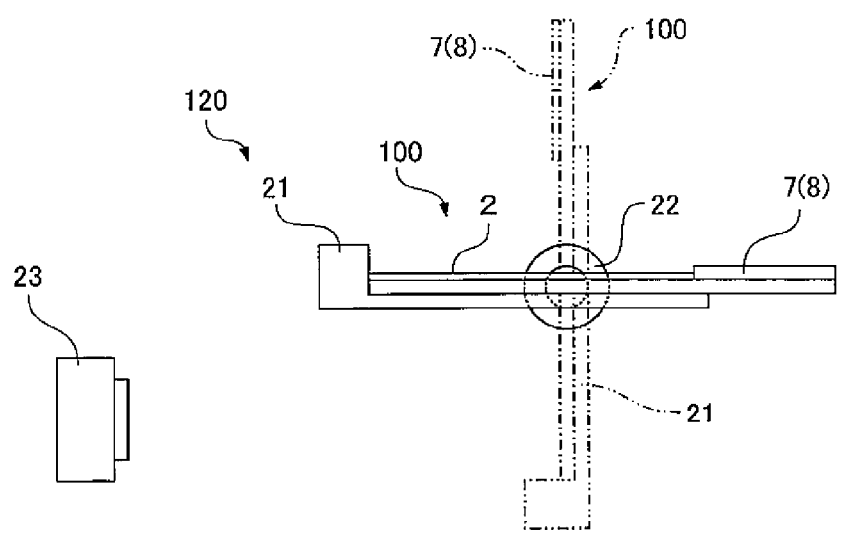

Next, an apparatus for analyzing a sample solution according to the embodiment 1 of the present invention will be described. FIGS. 2(a) and 2(b) are a plane view and a side view, respectively, schematically showing an example of the apparatus for analyzing a sample solution according to the embodiment 1 of the present invention.

As shown in FIGS. 2(a) and 2(b), an apparatus 120 for analyzing a sample solution includes: a holder 21 as a test strip holding unit which holds the test strip 100; a motor 22 as a shift driving unit which rotatably supports the holder 21; the image sensor 23 as a detecting unit which monitors (photographs) the test strip 100; and a controlling part (not shown) which controls the motor 22 based on the image or the like photographed by the image sensor 23. In this apparatus 120 for analyzing a sample solution, the test strip 100 is supported rotatably about an axis X along the width direction of the test strip 100, in the central part in the longitudinal direction of the test strip, though the present invention is not limited thereto.

Figure 3A:
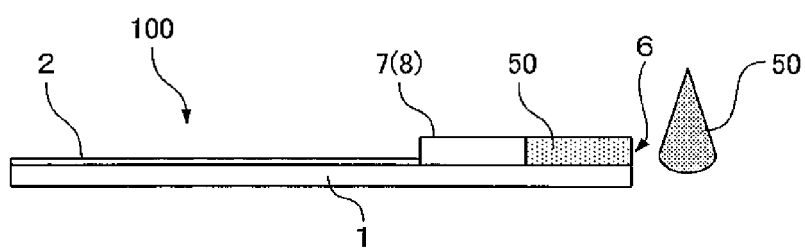
Figure 3B:
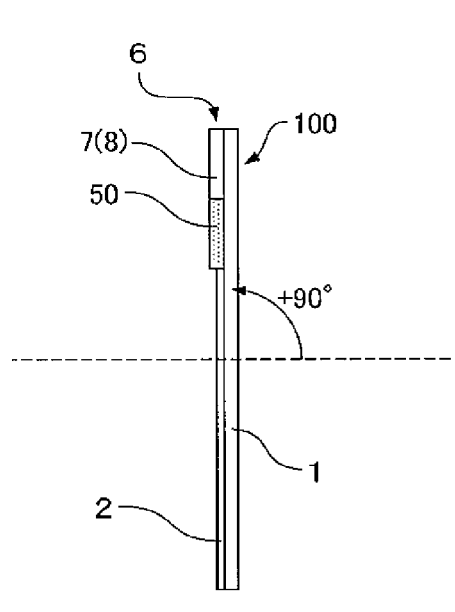
Figure 3C:
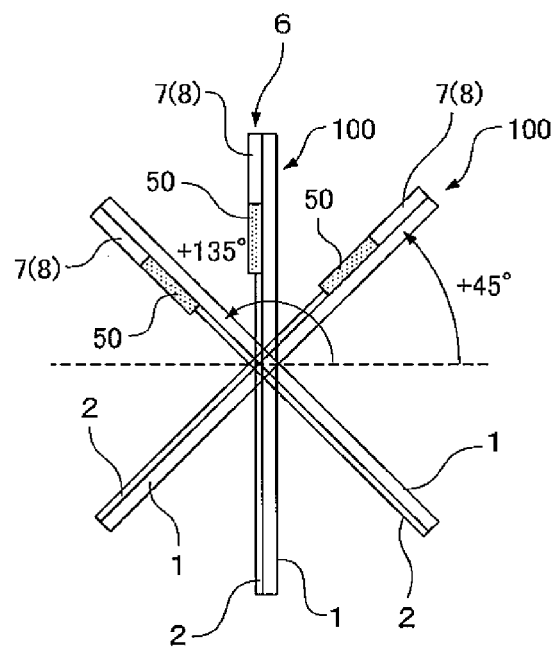

The method for analyzing a sample solution according to the present invention using such an apparatus 120 for analyzing a sample solution will be described below with reference to FIGS. 3(a) to 3(c). In this context, FIGS. 3(a) to 3(c) are respectively a side view schematically showing the method for analyzing a sample solution according to the embodiment 1 of the present invention, wherein FIG. 3(a) schematically shows a state during sample solution introduction in the method for analyzing a sample solution, and FIGS. 3(b) and 3(c) respectively schematically show a state during development in the method for analyzing a sample solution. For this method for analyzing a sample solution described below, it is preferable to use the apparatus 120 for analyzing a sample solution, though the present invention is not limited to the use of this apparatus 120 for analyzing a sample solution. An apparatus for analyzing a sample solution having a different constitution may be used, such as an apparatus 130 for analyzing a sample solution shown in FIGS. 7(a) to 7(c) described later. In the description below, an angle is defined with respect to the angle) (0°) of the test strip 100 disposed horizontally. An angle formed by counterclockwise rotation about the central part in the longitudinal direction of the test strip 100 with respect to this reference line is described as +, while an angle formed by clockwise rotation thereabout is described as −.

As shown in FIG. 3(a), first, the test strip 100 is held by the holder 21 so that the test strip 100 stands still in a horizontal posture (introduction posture). To the sample introduction part 6 in this test strip 100, a sample solution 50 is introduced, and the test strip 100 stands still in this horizontal posture for a predetermined time (e.g., 60 seconds) to favorably spread the sample solution 50 in the gap portion 8 in the test strip 100. The introduction posture of the test strip 100 during the introduction of the sample solution 50 to the sample introduction part 6 is not limited to standing still in a horizontal posture, and the test strip 100 may take any posture as long as the posture easily permits the procedure of introducing the sample solution 50 without a hitch. Then, as shown in FIG. 3(b), the test strip 100 is inclined +90° via the holder 21 to take such a development posture that the downstream region of the developing layer 2 faces downward and the space forming member 7 provided with the sample introduction part 6 faces upward to develop the sample solution to the developing layer 2. The test strip stands still in such a development posture, for example, for 240 seconds, and the degree of reaction on the test strip 100 is then measured using the image sensor 23.

Moreover, in this development posture, the sample solution is developed in the developing layer 2 through a capillary phenomenon, while a force is added by means of gravity to the sample solution 50 to move to the downstream region of the developing layer 2. Thus, the developing rate of the sample solution 50 is increased by means of gravity, compared with a test strip 100 kept in a horizontal posture. As a result, the development time or analysis time can be reduced. In addition, since the force is added by means of gravity to the sample solution 50 to move to the downstream region of the developing layer 2, not merely is the analysis time reduced, but also the developing rate is less susceptible to the viscosity of the sample solution 50 and thus has a small difference even among sample solutions 50 differing in viscosity, compared with a test strip 100 kept in a horizontal posture even during development. As a result, a sample solution (e.g., blood having an exceedingly large viscosity) arrives in almost equal amounts at a predetermined site (e.g., the reagent-immobilized part 4) in the developing layer 2, when measurement is performed with the analysis time set to a small amount of extra time (e.g., 40 seconds) added to a development time (e.g., 200 seconds) required for a sample solution 50 having a standard viscosity. Thus, the amount of the analyte passing through the reagent-immobilized part 4 within the analysis time does not differ among sample solutions. As a result, the analytical accuracy or reliability can be improved.

For example, when a predetermined substance is analyzed using blood as the sample solution 50, blood having a low viscosity (e.g., hematocrit (value having positive correlation with the viscosity of blood): approximately 20%) is developed at a distance of 1.3 times that of, for example, blood having a standard hematocrit of around 40%, in a test strip 100 kept in a horizontal posture even during development. By contrast, blood having a high viscosity (e.g., hematocrit: approximately 60%) is developed at a distance 0.7 times that of the blood in this test strip 100. Therefore, the amount of the predetermined substance passing through the reagent-immobilized part 4 also differs therebetween. Thus, when the concentration of the predetermined substance is measured using this test strip 100, the rate of deviation from the true value with respect to blood having a standard hematocrit of 40% is as large as +60% for blood having a hematocrit of approximately 20% and −60% for blood having a hematocrit of approximately 60%. By contrast, the test strip 100 inclined +90° so that the downstream region of the developing layer 2 faces downstream during the development as aforementioned exhibits a small difference in development distance between blood having a hematocrit of approximately 20% and blood having a hematocrit of approximately 60%. Therefore, the rate of deviation from the true value is also reduced almost 50%. Thus, the development is less susceptible to the viscosity of the sample solution 50.

Specifically, in the test strip 100 kept in a horizontal posture during development, it is highly possible that a portion of the sample solution 50 having a large viscosity dose not arrive at the predetermined position (reagent-immobilized part 4) even after a long time spent for the development. In such a case, the analytical accuracy or reliability may be reduced. By contrast, the present embodiment can minimize such a problem and can improve the analytical accuracy or reliability.

The posture of the test strip 100 during development (development posture) is more preferably a posture inclined +90° so that the downstream region of the developing layer 2 faces downward as aforementioned. However, the development posture is not limited thereto, and a development posture inclined at any angle, preferably +45 to +135°, as shown in FIG. 3(c) also has the effect of making the developing rate less susceptible to the viscosity of the sample solution. However, a posture inclined +30° or smaller or +150° or larger is not preferable because this posture hardly differs from the horizontal posture in their effects. Moreover, the time for which the test strip stands still in a horizontal posture (introduction posture) immediately after introduction and the time for which the test strip stands still in such a development posture that the downstream region of the developing layer 2 faces downward are not limited to the aforementioned times. The optimal times can be selected according to the property of the test strip 100.

Figure 4A:
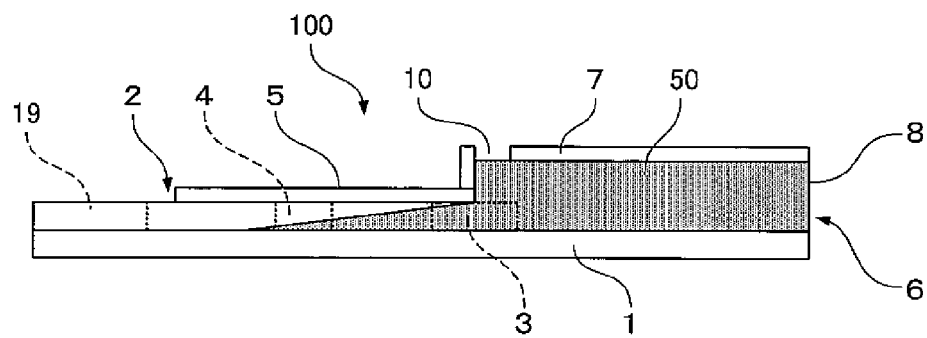
Figure 4B:
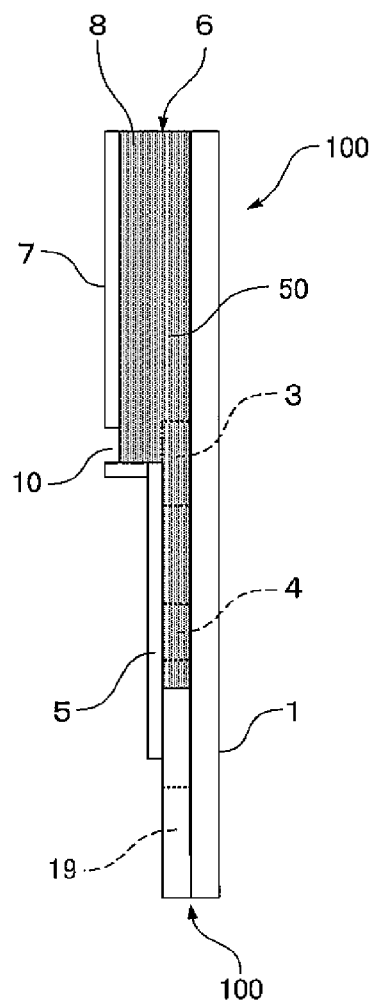

Moreover, the present embodiment also has advantages shown below, in addition to the aforementioned effect. In this context, FIGS. 4(a) and 4(b) are respectively a cross-sectional side view showing the state of the test strip 100 after a given time from the introduction of the sample solution 50 in this embodiment. FIG. 4(a) is a cross-sectional side view showing as a comparative example that the test strip continues to stand still in a horizontal posture even after the introduction of the sample solution 50, and FIG. 4(b) is a cross-sectional side view showing as the embodiment of the present invention that the test strip stands still in such a development posture that the downstream region of the developing layer 2 faces downward after the introduction of the sample solution 50.

As shown in FIG. 4(a), when the sample solution 50 as a sample to be measured is introduced to the sample introduction part 6 in the test strip 100 disposed in a horizontal posture and then the test strip 100 continues to stand still in this horizontal posture, the sample solution 50 is developed to the downstream region of the developing layer 2. During this development, the developing layer 2 has smaller friction on the developing layer support side (on the underside of the developing layer) than on the liquid-impermeable sheet side. Therefore, the sample solution 50 tends to be developed faster on the developing layer support 1 side due to the enhanced capillary phenomenon and developed slower on the liquid-impermeable sheet 5 side. Thus, in the test strip 100 disposed in a horizontal posture not only during introduction but also during development, the sample solution is developed non-uniformly in the thickness direction of the developing layer 2 (i.e., developed faster on the lower side and slower on the upper side in the thickness direction of the developing layer 2). As a result, a nonuniform reaction occurs in the reagent-immobilized part 4. Furthermore, this causes an indefinite boundary in the position of the development or variations in color intensity in the reagent-immobilized part. Therefore, the measurement of the degree of reaction on the test strip 100 using the image sensor 23 tends to result in deteriorated precision.

However, in the present embodiment, the test strip 100 shifted to the development posture (+45° to +135°) as aforementioned utilizes, in addition to the force of a capillary phenomenon, gravity further imparted thereto as a force developing the sample solution 50 in the direction of development, as shown in FIG. 4(b). Therefore, the sample solution 50 is developed to the downstream region of the developing layer 1 without a difference in developing rate between the developing layer support 1 side and the liquid-impermeable sheet 5 side. Accordingly, variations in the development of the sample solution 50 in the thickness and width directions of the developing layer 2 can be alleviated. As a result, the sample solution 50 is developed almost uniformly to the downstream region of the developing layer 2. Thus, the sample solution 50 reacts uniformly without variations in the thickness and width directions of the developing layer 2 with the labeling reagent in the labeling reagent holding part 3 or the immobilized reagent in the reagent-immobilized part 4. This also achieves uniform color intensity in the reagent-immobilized part 4 in the thickness and width directions. Accordingly, the measurement of the degree of reaction on the test strip 100 using the image sensor 23 is performed with higher precision, because the position of the development can be clearly observed.

Embodiment 2

Figure 5A:
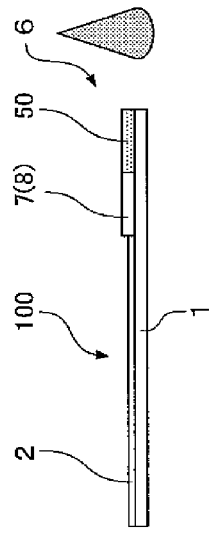
FIGS. 5(a) and 5(b) are respectively a side view schematically showing a state during sample solution introduction in a method for analyzing a sample solution according to an embodiment 2 of the present invention.
Figure 5B:
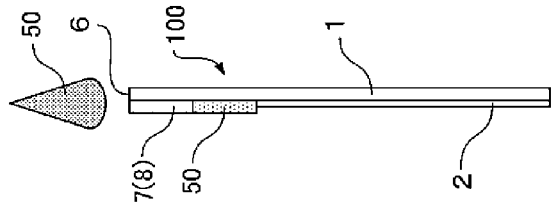
Figure 5C:
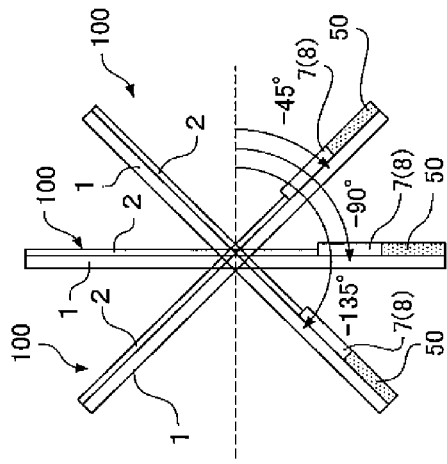
FIG. 5(c) is a side view schematically showing a state after sample solution introduction and before development in the method for analyzing a sample solution.
Figure 5D:
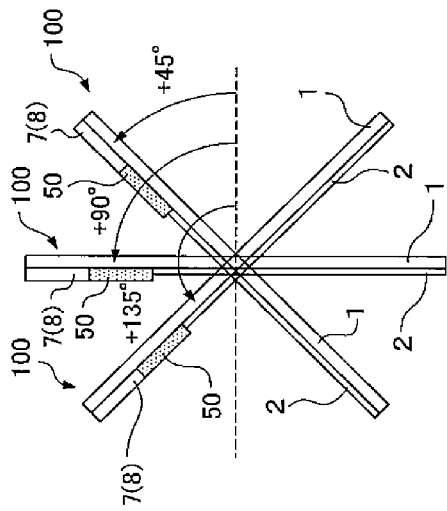
FIG. 5(d) is a side view schematically showing a state during sample solution development in the method for analyzing a sample solution.

FIGS. 5(a) and 5(b) are respectively a side view schematically showing a state during sample solution (blood) introduction in a method for analyzing a sample solution according to an embodiment 2 of the present invention, FIG. 5(c) is a side view schematically showing a state after sample solution introduction and before development in the method for analyzing a sample solution, and FIG. 5(d) is a side view schematically showing a state during sample solution development in the method for analyzing a sample solution. Moreover, FIGS. 6(a) to 6(c) are respectively an image of the behavior of red blood cells as a cellular component in a gap portion in the method for analyzing a sample solution, wherein FIG. 6(a) is a diagram schematically showing a state immediately after sample solution introduction, FIG. 6(b) is a diagram schematically showing a state after a lapse of some time after sample solution introduction, and FIG. 6(c) is a diagram schematically showing a state during sample solution development.

For the method for analyzing a sample solution according to the embodiment 1, the method for coping with the problem associated with the sample solution 50 development is described. However, the conventional method for analyzing a sample solution wherein the test strip 100 is kept in a horizontal posture even after sample solution introduction also has the problem of an insufficient reaction, because the sample solution 50 introduced in the test strip 100 is not favorably mixed with a reagent (e.g., a cell shrinkage reagent 9). The embodiment of the present invention described below also copes with this problem.

A test strip 100 used in the method for analyzing a sample solution according to this embodiment 2 is constituted in the same way as in those described in FIGS. 1(a), 1(b), 10(a), and 10(b). Specifically, the test strip 100 includes: a gap portion 8 formed by a transparent space forming member 7 which has an air vent 10 and holds a cell shrinkage reagent 9; a developing layer 2 which holds and immobilizes a labeling reagent and an antibody; a liquid absorption part 19 which finally absorbs a sample solution 50; a developing layer support 1 which supports the developing layer 2 and the liquid absorption part 19; and a transparent liquid-impermeable sheet 5 which protects the sample solution 50 (e.g., blood) from drying and assists in uniform development. A sample introduction part 6 which introduces the sample solution 50 therethrough is formed at the end of the gap portion 8 in the test strip 100. Thus, the sample introduction part 6 formed by an opening at the end of the gap portion 8 is provided on one side of the test strip 100. This gap portion 8 holds the cell shrinkage reagent 9. Moreover, the developing layer 2 is provided so that the downstream region of the developing layer 2 extends to the other side of the test strip 100. In this context, the air vent 10 formed in the space forming member 7 discharges the air of the gap portion 8 so that the sample solution 50 is smoothly aspirated in the gap portion 8 during the introduction of the sample solution 50.

Next, the method for analyzing a sample solution according to this embodiment 2 will be described with reference to FIGS. 5(a) to 5(d) and 6(a) to 6(c).

Blood is introduced as the sample solution 50 to the sample introduction part 6 at the end of the gap portion 8 in the test strip 100. During this introduction, the test strip 100 may be disposed in an introduction posture suitable for introducing the sample solution 50 to the sample introduction part 6. The introduction posture may be, for example, a posture in which the test strip 100 stands still horizontally as shown in FIG. 5(a) or a posture in which the sample introduction part 6 in the test strip 100 faces upward as shown in FIG. 5(b).

After the blood introduction to the sample introduction part 6 in the test strip 100, the test strip 100 is put into standby mode in such a posture inclined −45° to −135° that the sample introduction part 6 on the one side of the test strip 100 is positioned lower than the downstream region of the developing layer 2 on the other side of the test strip 100 as shown in FIG. 5(c). This posture permits a sufficient reaction with the cell shrinkage reagent 9 as described later and hereinafter, is referred to as a reaction posture. An angle formed by this reaction posture is most preferably −90°, though the angle is not limited thereto. This angle may be any angle from −45° to −135°.

A test strip 100 standing still along the horizontal direction after sample solution 50 introduction as in the conventional method for analyzing a sample solution exhibits variations in the concentrations of blood and the cell shrinkage reagent 9 in the gap portion 8. As a result, red blood cells insufficiently reacted with the cell shrinkage reagent 9 are developed to the developing layer 2. By contrast, in the test strip 100 put into standby mode in a reaction posture inclined −45° to −135° as in the present embodiment, red blood cells 11 in blood introduced through the sample introduction part 6 are moved by means of gravity to the sample introduction part 6 (distantly from the developing layer 2) on the one side of the test strip 100 as shown in FIG. 6(a), or stay in the gap portion 8. This is because components of red blood cells usually have larger gravity (generally 1.095) than that (generally 1.025 to 1.029) of plasma components in human blood, though there are variations among individuals. Accordingly, a time for which the red blood cells 11 stay in the gap portion 8 can be secured. As a result, the red blood cells 11 in blood react uniformly without variations with the cell shrinkage reagent 9 and are thereby contracted into a size smaller than the pores of the developing layer 2 made of a porous carrier (i.e., the state of red blood cells 11' shown in FIG. 6(a)).

When the test strip 100 is kept in this posture, a portion of blood (represented by reference numeral 12 in FIG. 6(b)) is developed to the developing layer 2 as shown in FIG. 6(b). However, when blood held in the gap portion 8 becomes smaller in volume than the gap portion 8, a fluid level 50a of the blood is positioned lower than the end of the developing layer 2 so that the blood in the gap portion 8 does not have contact with the developing layer 2 any more. As a result, the blood is not developed to the developing layer 2. Therefore, the test strip 100 is disposed in the reaction posture for 30 seconds (which probably permits a sufficient reaction) and then kept in such a posture inclined +45° to +135° (development posture) that the downstream region of the developing layer 2 on the other side of the test strip 100 is positioned lower than the sample introduction part 6 on the one side of the test strip 100 as shown in FIG. 5(d). An angle formed by this development posture is most preferably +90°, though the angle is not limited thereto. This angle may be any angle from +45° to +135°.

Accordingly, blood flows to the downstream region of the developing layer 2 by means of gravity as shown in FIG. 6(c) and therefore moves from the sample introduction part 6 side to the air vent 10 side in the gap portion 8 to come in contact with the developing layer 2. As a result, blood (sample solution 50) containing sufficiently contracted red blood cells 11' is developed to the developing layer 2. Moreover, the residues of blood in the gap portion 8 can be eliminated by the effect of the gravity imparted thereto. Then, an analyte in blood reacts with the labeling reagent and an immobilized reagent. As a result, a color of the labeling reagent appears in a reagent-immobilized part 4. The appearing color of the labeling reagent is measured as color intensity by a signal from an image sensor 23 to favorably and accurately detect the presence or concentration of the analyte.

According to the method for analyzing a sample solution according to this embodiment, since the red blood cells 11 in blood react sufficiently and uniformly with the cell shrinkage reagent 9 in the gap portion 8 and are then developed to the developing layer 2, blood can react with the labeling reagent and a labeled antibody without clogging the developing layer 2. Furthermore, since blood does not remain in the gap portion 8, the sample solution 50 even in trace amounts can be measured highly precisely. Moreover, in this embodiment as well, the developing rate is less susceptible to the viscosity of the sample solution 50 by virtue of the development posture during development, as in the embodiment 1. As a result, the analytical accuracy or reliability can be improved.

Figure 7A:
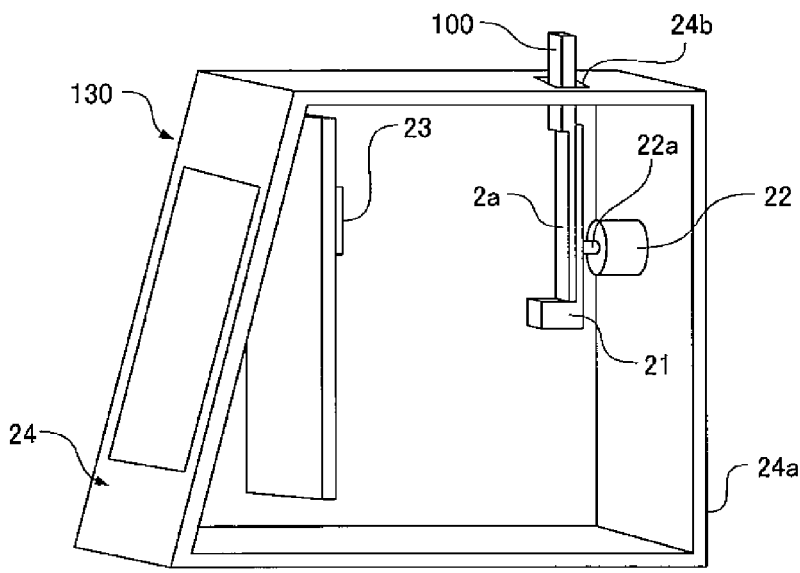
Figure 7B:
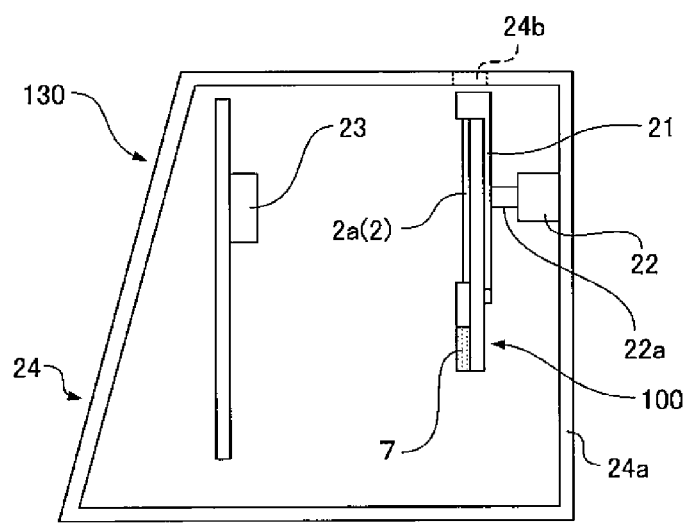
Figure 7C:
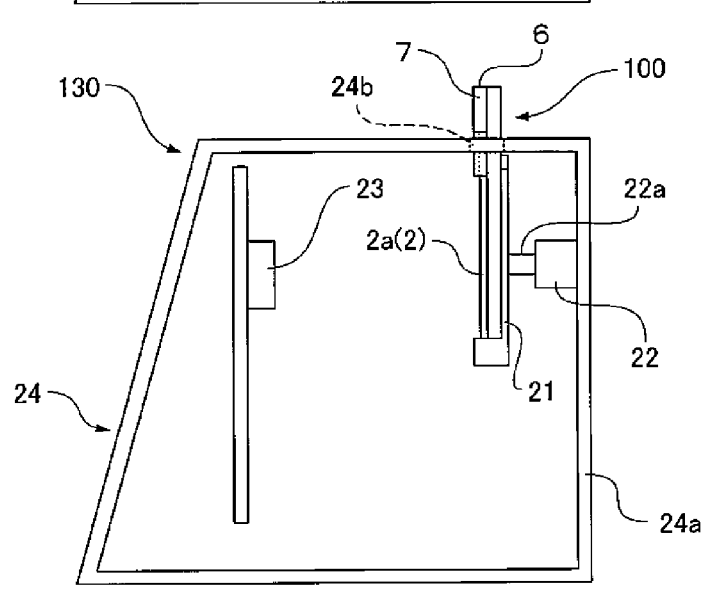

In this context, an apparatus 130 for analyzing a sample solution shown in FIGS. 7(a) to 7(c) may be used, instead of the apparatus 120 for analyzing a sample solution shown in FIGS. 2(a) and 2(b), in the method for analyzing a sample solution according to this embodiment.

Next, FIGS. 7(a) to 7(c) are respectively a diagram schematically showing the structure of the apparatus 130 for analyzing a sample solution according to the embodiment 2 of the present invention, wherein FIG. 7(a) is a perspective view of the apparatus 130 for analyzing a sample solution, FIG. 7(b) is a side view of the apparatus 130 for analyzing a sample solution immediately after blood introduction, and FIG. 7(c) is a side view of the apparatus 130 for analyzing a sample solution after changing an angle at which a test strip is inclined. The same reference numerals will be used to designate components having the same or similar functions as those in the apparatus 120 for analyzing a sample solution shown in FIGS. 2(a) and 2(b).

As shown in FIGS. 7(a) to 7(c), the apparatus 130 for analyzing a sample solution includes: a holder 21 as a test strip holding unit which holds a test strip 100; a motor 22 as a shift driving unit which rotatably supports the holder 21; an image sensor 23 which monitors (photographs) the test strip 100; a controlling part (not shown) which controls the motor 22 based on the image or the like photographed by the image sensor 23; and a case 24 which accommodates these holder 21, motor 22, image sensor 23 and controlling part. In this apparatus 130 for analyzing a sample solution, the motor 22 is mounted in such a posture on the inner surface of a back panel 24a of the case 24 that a rotation axis 22a of the motor is positioned horizontally. The holder 21 mounted to the rotation axis 22a and the test strip 100 attached to this holder 21 are arranged to rotate in a plane (referred to as a plane for detection) 2a (in this embodiment, in a vertical plane orthogonal to the horizon) in which the state of development in a developing layer 2 in the test strip 100 can be determined and detected. A long hole 24b is formed in the top panel of the case 24 so that a site positioned at the upper end of the test strip 100 protrudes from the long hole 24b. Moreover, the image sensor 23 is arranged to face the plane 2a for detection of the developing layer 2 in the test strip 100.

During blood introduction, the motor 22 is positionally controlled to dispose the holder 21 in a posture shown in FIG. 7(a). To this holder 21, a test subject or the like loads (attaches) the test strip 100. Accordingly, the test strip 100 is held in such a posture that the sample introduction part 6 protrudes from the top panel of the case 24 as shown in FIG. 7(a). In this state, the test subject or the like introduces blood to the sample introduction part 6.

In the apparatus 130 for analyzing a sample solution, the test strip 100 is loaded, while the image sensor 23 is controlled to start to monitor the test strip 100. When the apparatus automatically recognizes the blood introduction to the test strip 100 by image processing, the motor 22 rotates the test strip 100 at an angle of 180° so that the sample introduction part 6 in the test strip 100 is positioned lower than the downstream region of the developing layer 2 (reaction posture) as shown in FIG. 7(b). This rotation may be performed in any direction. Moreover, during this operation, the image sensor 23 further monitors the test strip 100 and detects a position 50b at which blood arrives in the developing layer 2 as shown in FIG. 8.

The controlling part in the apparatus 130 for analyzing a sample solution confirms that the position 50b at which blood arrives reaches a predetermined distance L or larger from the end of the test strip 100 provided with the sample introduction part 6. After a lapse of any time, the motor 22 rotates the test strip 100 at an angle of 180° so that the test strip 100 is disposed in such a development posture that the downstream region of the developing layer 2 is positioned lower than the sample introduction part 6 as shown in FIG. 7(c). Then, after a lapse of a predetermined time (e.g., 5 minutes) from blood introduction, the image sensor 23 photographs the test strip 100 disposed in this development posture and measures the color intensity of the reagent-immobilized part 4. As a result, the concentration of an analyte in blood is detected.

According to the apparatus 130 for analyzing a sample solution according to this embodiment, since the test strip 100 is arranged to rotate in the same plane as the plane 2a for detection of the developing layer 2, the surface state of the test strip 100 can always be monitored by one image sensor 23. Moreover, in this case, since the image sensor 23 necessary for the measurement can also be used in the detection of timing of changing an angle at which the test strip 100 is inclined, another special part is unnecessary. Thus, the apparatus according to this embodiment advantageously offers reduced production cost and simplified assembly procedures.

In this context, the apparatus 120 for analyzing a sample solution shown in FIGS. 2(a) and 2(b) may be used instead of this apparatus 130 for analyzing a sample solution. In this case, the test strip 100 during blood introduction may be disposed in the horizontal posture as shown in the solid line in FIG. 2(b) or may be disposed so that the sample introduction part 6 in the test strip 100 faces upward as shown in the imaginary line in FIG. 2(b). Thus, the test strip 100 is preferably disposed in a posture that permits easy blood introduction.

Embodiment 3

Next, a method for analyzing a sample solution using plasma as the sample solution will be described with reference to FIGS. 1, 5, and 9. This plasma used as a sample solution 50 is free from red and white blood cells. Therefore, a test strip 100 having the same constitution as that shown in FIG. 1(a) is used in this method except that the test strip 100 has no cell shrinkage reagent 9 as shown in FIG. 1(b).

Figure 9A:
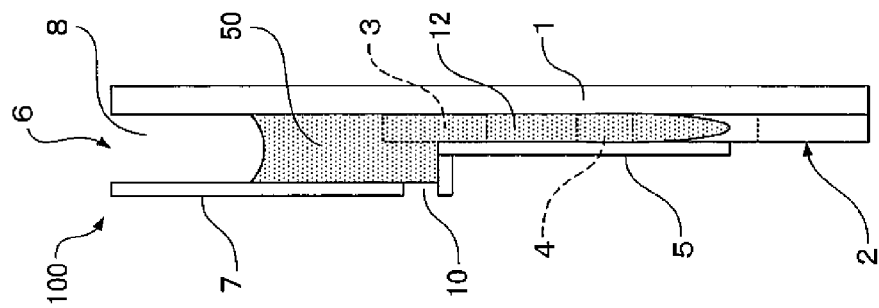
FIG. 9(a) shows the mixed state of plasma and the labeling reagent immediately after plasma introduction.
Figure 9B:
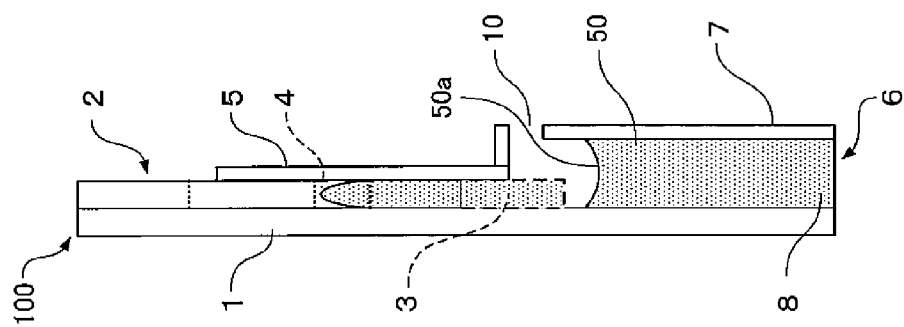
FIG. 9(b) shows the mixed state after a lapse of some time after plasma introduction.
Figure 9C:
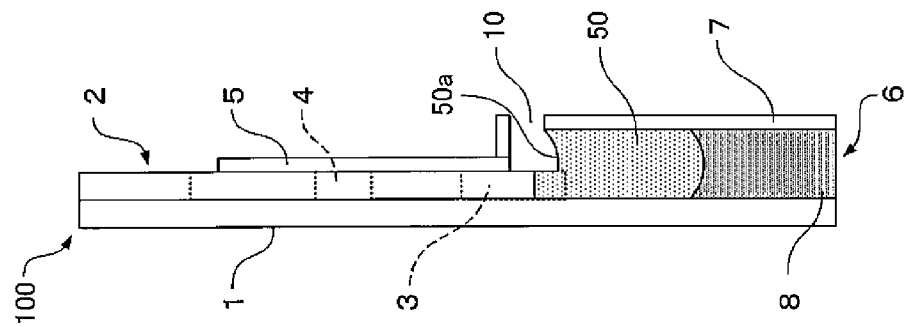
FIG. 9(c) shows a state during development.

FIGS. 9(a) to 9(c) are respectively an image of the mixed state of plasma as a sample solution 50 and a labeling reagent in a gap portion 8 in the test strip 100 according to this embodiment 3, wherein FIG. 9(a) is a diagram showing the mixed state of plasma and the labeling reagent immediately after plasma introduction, FIG. 9(b) is a diagram schematically showing the mixed state after a lapse of some time after plasma introduction, and FIG. 9(c) is a diagram schematically showing a state during development.

First, plasma is introduced to a sample introduction part 6 at the end of the gap portion 8 in the test strip 100. During this plasma introduction, the test strip may be disposed in an introduction posture (not shown) suitable for introducing the sample solution 50 to the sample introduction part 6, as in the embodiment 2. The introduction posture may be, for example, a posture in which the test strip 100 stands still horizontally as shown in FIG. 5(a) or a posture in which the sample introduction part 6 in the test strip 100 faces upward as shown in FIG. 5(b). Then, the test strip 100 is put into standby mode in such a reaction posture inclined −45° to −135° that the sample introduction part 6 on one side of the test strip 100 is positioned lower than the downstream region of a developing layer 2 on the other side of the test strip 100 as shown in FIG. 5(c). An angle formed by this reaction posture is most preferably −90°, though the angle is not limited thereto. This angle may be any angle from −45° to −135°. Moreover, FIG. 9(a) shows a state at −90°.

The test strip 100 standing still along the horizontal direction after plasma introduction as in the conventional method for analyzing a sample solution exhibits variations in the concentration of the labeling reagent eluted into plasma in the gap portion 8. As a result, plasma insufficiently reacted with the labeling reagent is developed to the developing layer 2. By contrast, in the test strip 100 put into standby mode in a reaction posture inclined −45° to −135° as in the present embodiment, plasma is moved by means of gravity to the sample introduction part 6 (distantly from the developing layer 2) on the one side of the test strip 100 as shown in FIG. 9(a), or stays in the gap portion 8. Accordingly, a time for which plasma stays in the gap portion 8 can be secured. As a result, plasma reacts uniformly without variations with the labeling reagent.

When the test strip 100 is kept in this posture, a portion of plasma is developed to the developing layer 2 as shown in FIG. 9(b). However, when plasma held in the gap portion 8 becomes smaller in volume than the gap portion 8, a fluid level 50a of plasma is positioned lower than the end of the developing layer 2, so that the plasma in the gap portion 8 does not have contact with the developing layer 2 any more. As a result, the plasma is not developed to the developing layer 2. Therefore, in this embodiment, the test strip 100 is disposed in the reaction posture for 30 seconds (which probably permits a sufficient reaction) and then kept in such a development posture inclined +45° to +135° that the downstream region of the developing layer 2 on the other side of the test strip 100 is positioned lower than the sample introduction part 6 on the one side of the test strip 100 as shown in FIG. 9(c). Accordingly, the plasma flows by means of gravity to the downstream region of the developing layer 2 as shown in FIG. 9(c) and thereby moves from the sample introduction part 6 side to the air vent 10 side in the gap portion 8 to come in contact with the developing layer 2. As s result, plasma sufficiently reacted with the labeling reagent is developed to the developing layer 2. Moreover, the residues of plasma in the gap portion 8 can be eliminated by the effect of the gravity imparted thereto. Then, an analyte in plasma reacts with the labeling reagent and is then immobilized in a reagent-immobilized part 4. A color of the labeling reagent appearing in the reagent-immobilized part 4 is measured as color intensity by a signal from an image sensor 23 to favorably and accurately detect the presence or concentration of the analyte.

According to the method for analyzing a sample solution according to this embodiment, since plasma reacts with the labeling reagent sufficiently and uniformly in the gap portion 8 and is then developed to the developing layer 2 and since no plasma remains in the gap portion 8, the sample solution 50 even in trace amounts can be measured highly precisely. Moreover, in this embodiment as well, the developing rate is less susceptible to the viscosity of the sample solution 50 by virtue of the development posture during development, as in the embodiment 1. As a result, the analytical accuracy or reliability can be improved.

In these embodiments 2 and 3, the test strip 100 is disposed in such a reaction posture that the sample introduction part 6 faces downward, and the test strip 100 is then shifted to such a development posture that the downstream region of the developing layer 2 faces downward. After a predetermined time, the image sensor 23 detects the presence or concentration of the analyte, as aforementioned. However, the present invention is not limited thereto, and the operation of disposing the test strip 100 in the reaction posture after the introduction of the sample solution 50 thereto and then the operation of shifting the test strip to the development posture may be performed repetitively.

By repetitively performing the operation of disposing the test strip in the reaction posture and the operation of shifting the test strip to the development posture in this way, the cell shrinkage reagent 9 or the labeling reagent and the sample solution 50 are more favorably stirred, compared with a reaction between a cell shrinkage reagent 9 or a labeling reagent and a sample solution 50 in a test strip kept in the reaction posture. As a result, the effect of providing a further favorable reaction therebetween can be achieved.

In the embodiments 1 to 3, the sample solution does not have contact with the developing layer 2 any more in the test strip shifted to the reaction posture, as aforementioned. However, the present invention is not limited thereto, and these embodiments are sufficiently effective even for a structure where the sample solution 50 always comes in contact with a portion of the developing layer 2 in such a way that the developing layer 2 extends to the sample introduction part 6.

Moreover, the duration of the reaction posture may be any time, and it is preferable to select the optimum duration for each embodiment.

Furthermore, the timing of changing the posture of the test strip 100 (changing the angle at which the test strip 100 is inclined) may be detected based on the position of the fluid level of the sample solution 50 held in the gap portion 8 described in FIG. 6(*b*) and may be detected by any method.

Furthermore, the shift driving unit which changes the posture of the test strip 100 (changes the angle at which the test strip 100 is inclined) or a method therefor may be any unit or method. A method for measuring the lapse of time may be any method.

Furthermore, the test strip 100 is monitored using the image sensor 23 in the methods aforementioned. However, the monitoring may be performed by any method.

Furthermore, the color intensity is measured by photographing using the image sensor 23 and image processing in the methods aforementioned. However, the measurement may be performed by any method.

Furthermore, examples of the sample solution 50 that may be used include blood as well as other sample solutions including those containing cells (e.g., bacterial solutions) and body fluids (e.g., urine, serum, and saliva). Moreover, biological materials such as proteins, hormones, bacteria, and viruses contained in those sample solutions may be measured as an analyte. Specific examples of the analyte include analytes for water examination, human chorionic gonadotropin in urine, various antibodies and antigens in blood, albumin, HbAlc, estradiol, estriol, corpus luteum hormone, and bacteria or viruses contained in saliva in the mouth.

INDUSTRIAL APPLICABILITY

A method for analyzing a sample solution and an apparatus for analyzing a sample solution according to the present invention achieve highly precise measurement of a sample solution even in trace amounts and is therefore suitable particularly when rapid, convenient, accurate and highly precise measurement of an analyte is required.

The invention claimed is:

1. A method for analyzing a sample solution contained in a test strip, wherein the test strip comprises a sample introduction part located at a first end of the test strip and a developing layer disposed downstream of the sample introduction part and extending toward a second end of the test strip that is opposite to the first end, a reagent being disposed adjacent the first end of the test strip, the method comprising:

shifting the test strip to a reaction posture during or after introduction of a sample solution through the sample introduction part, in which the first end of the test strip is positioned lower than the second end of the test strip;

maintaining the test strip in the reaction posture;

mixing the reagent with the sample solution in the reaction posture by moving the sample solution to or keeping the sample solution at the first end of the test strip by means of gravity;

shifting the test strip to a development posture, in which the second end of the test strip is positioned lower than the first end of the test strip;

maintaining the test strip in the development posture, thereby allowing the sample solution mixed with the reagent to develop on the developing layer through both a capillary phenomenon and gravity; and analyzing an analyte contained in the sample solution in the developing layer.

2. The method for analyzing a sample solution according to claim 1, further comprising: disposing the test strip in an introduction posture suitable for introducing the sample solution to the sample introduction part before shifting the test strip to the reaction posture+−.

3. The method for analyzing a sample solution according to claim 1, wherein the operation of disposing the test strip in the reaction posture after the introduction of the sample solution thereto and then the operation of shifting the test strip to the development posture are repetitively performed.

4. The method for analyzing a sample solution according to claim 1, further comprising changeably arranging posture of the test strip, detecting a position at which the sample solution arrives in the developing layer, and setting at least one of the posture of the test strip and duration of the posture based on the position.

5. The method for analyzing a sample solution according to claim 1, wherein the sample solution is blood.

* * * * *